(12) United States Patent
Turconi et al.

(10) Patent No.: US 10,548,758 B2
(45) Date of Patent: Feb. 4, 2020

(54) MULTIFUNCTIONAL HIP BRACE

(71) Applicant: ORTHOSERVICE AG, Chiasso (CH)

(72) Inventors: Francesco Turconi, Monza (IT); Paolo Rossi, Morbio Inferiore (CH)

(73) Assignee: ORTHOSERVICE AG, Chiasso (CH)

( * ) Notice: Subject to any disclaimer, the term of this patent is extended or adjusted under 35 U.S.C. 154(b) by 449 days.

(21) Appl. No.: 15/424,103

(22) Filed: Feb. 3, 2017

(65) Prior Publication Data

US 2017/0216076 A1  Aug. 3, 2017

(30) Foreign Application Priority Data

Feb. 3, 2016  (IT) ................. 10201611006

(51) Int. Cl.
*A61F 5/01* (2006.01)
*A61F 7/00* (2006.01)

(52) U.S. Cl.
CPC .......... *A61F 5/0193* (2013.01); *A61F 5/0102* (2013.01); *A61F 7/00* (2013.01); *A61F 2007/004* (2013.01)

(58) Field of Classification Search
CPC .................. A61F 5/0193; A61F 5/0104; A61F 2005/0181; A61F 2005/0183; A61F 5/0102; A41D 13/0525; A41D 13/0543
See application file for complete search history.

(56) References Cited

U.S. PATENT DOCUMENTS 1,063,922 A * 6/1913 Kendrick ................. A41C 1/10
450/130

5,840,050 A * 11/1998 Lerman ................. A61F 5/0193
602/19

(Continued)

OTHER PUBLICATIONS

Italian Search Report dated Sep. 20, 2016 in Italian Application UB20160005 filed on Feb. 3, 2016 (with English Translation of Categories of Cited Documents).

*Primary Examiner* — Kari K Rodriquez
(74) *Attorney, Agent, or Firm* — Oblon, McClelland, Maier & Neustadt, L.L.P.

(57) ABSTRACT

A multifunctional hip brace comprises a retaining wrapping base of elastic fabric (12) comprising a side portion (13), a lumbar band (14a) and a thigh band (14b), wherein the lumbar band (14a) and the thigh band (14b) are placed at opposite ends of the side portion (13) and can be wrapped about the waist and about a thigh of the patient and can be clamped in adjustable positions through quick hooking means (16), wherein the side portion (13) is entirely made of fabric and wherein the elastic retaining wrapping base (12) comprises a plurality of arrangements (17', 17") for hooking additional accessory elements (18', 18") for selectively limiting the movements of the hip joint, such as an articulated rod (18'), said plurality of arrangements (17', 17") being externally constrainable in a removable manner to the side portion (13) through quick hooking means (19), and a pair of elastic pulling strips (18") externally constrainable in a removable manner through quick hooking means (19), diagonally placed between the lumbar band (14a) and the thigh band (14b) in a position crossed to one another, wherein the plurality of first and second arrangements (17', 17") for hooking the additional accessory elements (18', 18") are arranged longitudinally along the side portion (13) and frontally and rearly on the lumbar band (14a) and on the thigh band (14b).

8 Claims, 8 Drawing Sheets

(56) References Cited

U.S. PATENT DOCUMENTS

| | | |
|---|---|---|
| 2007/0027419 A1 | 2/2007 | Drennan |
| 2010/0292622 A1 | 11/2010 | Weissleder et al. |
| 2011/0092866 A1 | 4/2011 | Lartonoix |
| 2014/0207041 A1* | 7/2014 | Ingimundarson ..... A61F 5/0193 602/23 |

* cited by examiner

MULTIFUNCTIONAL HIP BRACE

BACKGROUND

The present invention relates to a multifunctional hip brace.

Hip braces consisting of a wrapping structure of elastic fabric provided with a lumbar band and with a thigh band adapted to be wrapped and closed about the waist and about a thigh (either right or left) of a patient are typically used for the post-surgical treatment of the hip or for the instability control of the femoroacetabular joint even in patients that have not undergone surgery. Such elastic hip braces are hereinafter referred to as "light hip braces" or simply as hip braces.

US 2010/0292622 A1 document shows an example of a light hip brace according to the preamble of claim 1, entirely made of elastic fabric, specifically devoid of rigid rod elements.

Other light hip braces may at most be laterally provided with one or more spiral stays, which are incorporated in the elastic fabric and which differ from the more complex and bulky rigid hip braces consisting of rigid lumbar and thigh shells joined by an articulated rod and that find application in particular in traditional post-surgery.

Light hip braces, though helping reducing the post-surgical edema, particularly in arthroscopic surgery, are often deemed to be insufficient, in particular as regards the control of the position of the joint and of the movements.

However, the spread of hip arthroscopy surgery has made these light braces particularly interesting, provided that they solve the need for movement control.

BRIEF SUMMARY

An object of the present invention is to make a multifunctional hip brace that solves the drawbacks of the prior art.

Another object of the present invention is to make a multifunctional hip brace capable of reducing the post-surgical edema and selectively limiting the abduction and flexion-extension movements in order to protect the joint subjected to surgery.

Another object of the present invention is to make a multifunctional hip brace that is particularly simple, functional and cost-effective.

These objects according to the present invention are achieved by making a multifunctional hip brace as outlined in claim 1.

Further features are provided in the dependent claims.

BRIEF DESCRIPTION OF THE DRAWINGS

The features and advantages of a multifunctional hip brace according to the present invention will become clearer from the following exemplifying and non-limiting description, referred to the enclosed schematic drawings, in which:

FIG. 1 shows a front view of a multifunctional hip brace according to the invention, which two crossed elastic pulling strips are applied to;

DETAILED DESCRIPTION

With reference to the figures, a multifunctional hip brace is shown, wholly indicated with reference number 10, comprising a retaining wrapping base of breathable elastic fabric 12, comprising a side portion 13, a lumbar band 14a, a thigh band 14b, as well as a lumbar closing support 15a and a thigh closing support 15b.

The lumbar band 14b and the thigh band 15b extend starting from opposite ends, upper and lower, of a side of the side portion 13 and each of them can be wrapped respectively about the waist and about a thigh of the patient and can be clamped on the relative closing supports 15a and 15b that extend starting from opposite ends, upper and lower, of a side of the side portion 13 opposite with respect to the lumbar band 14a and to the thigh band 14b.

The lumbar band 14a and the thigh band 14b can be clamped according to a plurality of continuously adjustable positions by means of quick hooking means 16, such as for example of the Velcro® type, placed at the ends thereof. In this case, the Velcro® quick hooking means 16 are hooked on corresponding portions of fabric sewed on the lumbar 15a and thigh 15b closing supports.

The hip brace 10 according to the invention is made specifically for the treatment of a left hip (FIGS. 1-2) or right hip (FIG. 3) and in the two embodiments has a mirror configuration.

The side portion 13 is entirely made of fabric, i.e. of soft and flexible material, and is not indissolubly connected to rigid elements, such as articulated rods or stays. In fact, there are no articulated rods or stays permanently constrained to it, for example embedded in non-removable manner in an inner pocket.

The elastic retaining wrapping base 12 of the brace 10 according to the invention comprises a plurality of hooking arrangements 17', 17" for additional accessory elements 18', 18" for selectively limiting the movements of the hip joint.

Figure 1:
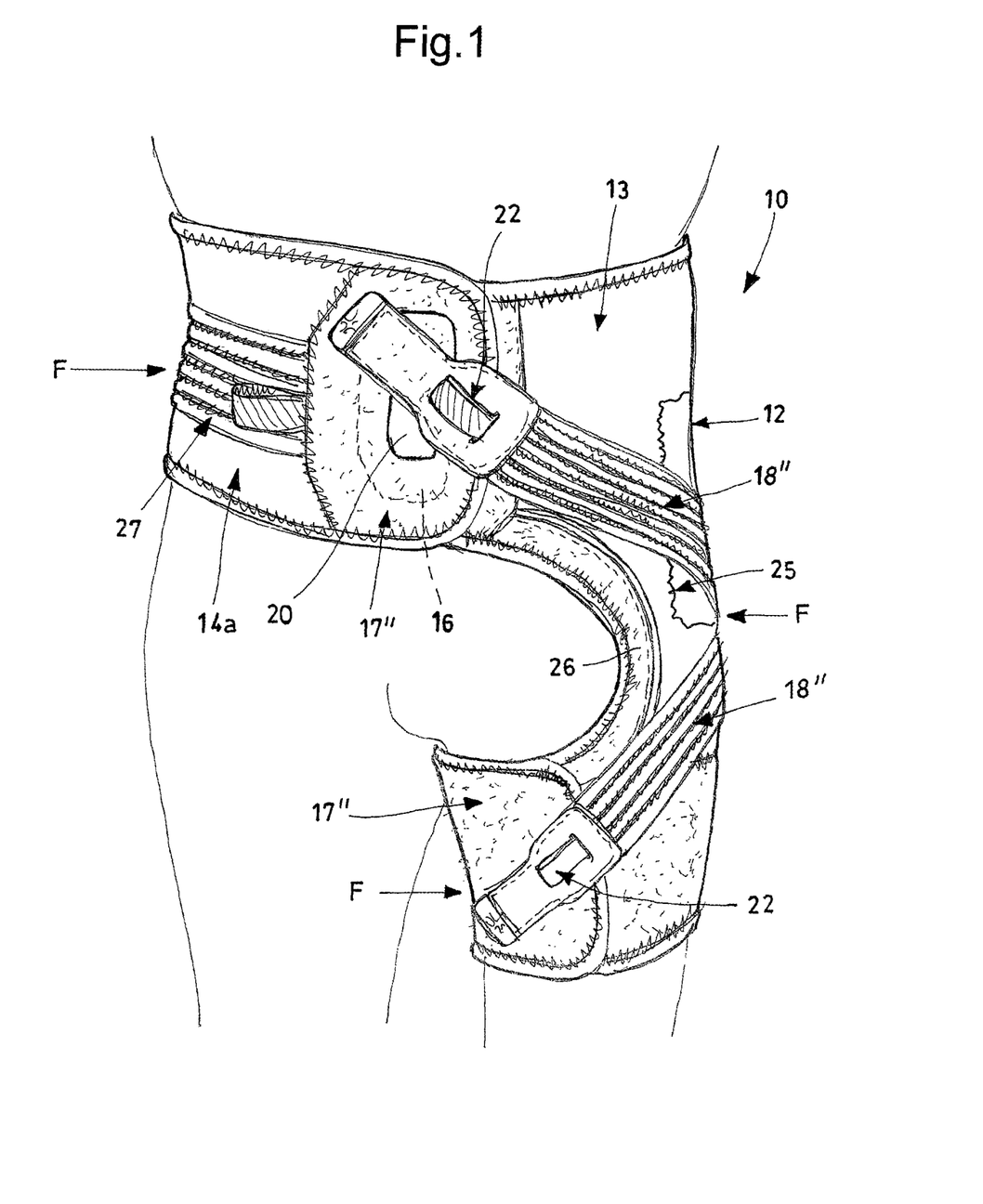
Figure 2:
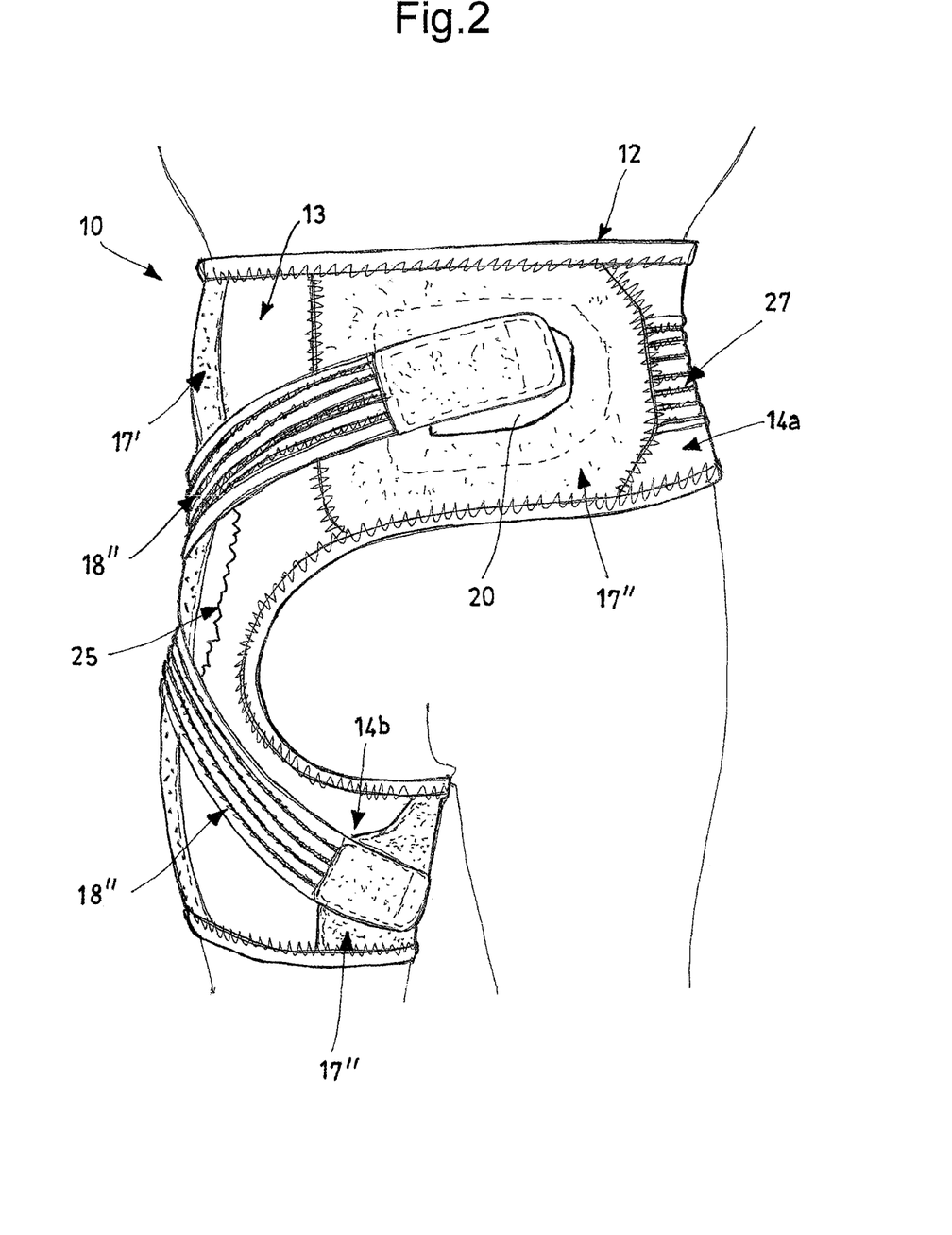
FIG. 2 shows a rear view of the brace of FIG. 1.

The hooking arrangements 17', 17" for additional accessory elements 18', 18" are first hooking arrangements 17' arranged longitudinally along the side portion 13 and second hooking arrangements 17" arranged on the brace 10 in two distinct points of the lumbar band 14a and in two distinct points of the thigh band 14b, so that when the brace is worn, the second hooking arrangements 17" are in front and rear position both on the lumbar band 14a and on the thigh band 14b (FIGS. 1 and 2).

According to the invention, the additional accessory elements present in the brace 10 are an articulated rod 18', which is externally constrainable to the side portion 13 by means of quick hooking means 19, and a pair of elastic pulling strips 18", which are externally constrainable by means of quick hooking means 19, diagonally between the lumbar band 14a and the thigh band 14b in a position crossed to one another.

Figure 3:
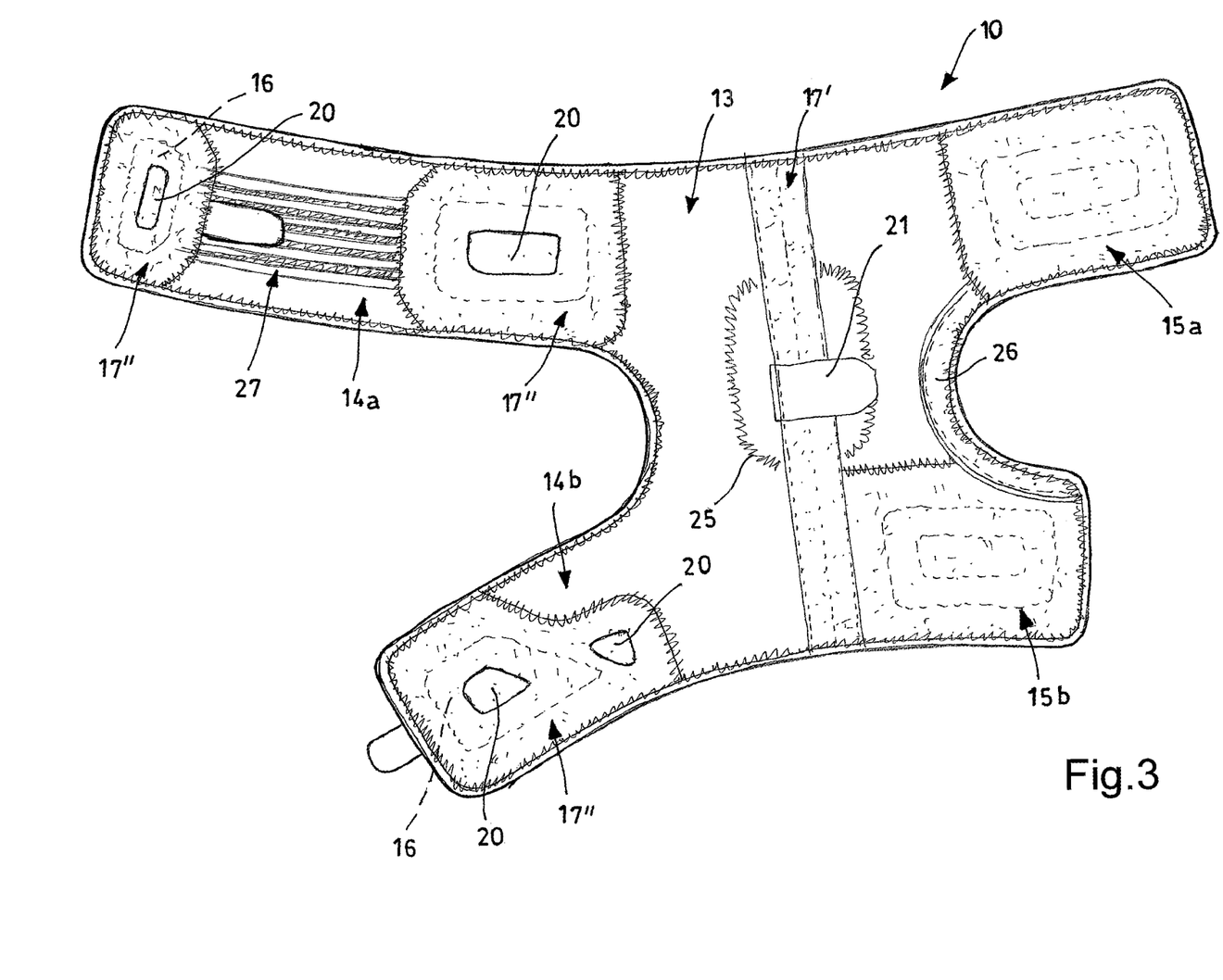
FIG. 3 shows a plan view of a multifunctional hip brace according to the invention in the right version.

According to the preferred embodiment shown, the second hooking arrangements 17" for hooking the pair of elastic pulling strips 18" consist of fabric portions for the adhesion of quick hooking means 19 of the Velcro® type. The fabric portions are arranged with indicators of the adhesion area 20 in order to ensure a correct positioning of the pair of pulling strips 18" by the user. The first hooking arrangements 17' for the articulated rod 18' comprise fabric portions for the adhesion of quick hooking means 19 of the Velcro® type and a central through 21 (FIG. 3).

Preferably, in order to effectively exert the retaining action of the joint movement, it has been seen that each of the elastic pulling strips 18" of the pair of elastic pulling strips of the brace 10 of the invention must exert a minimum force equal to 30-35 N.

Figure 4:
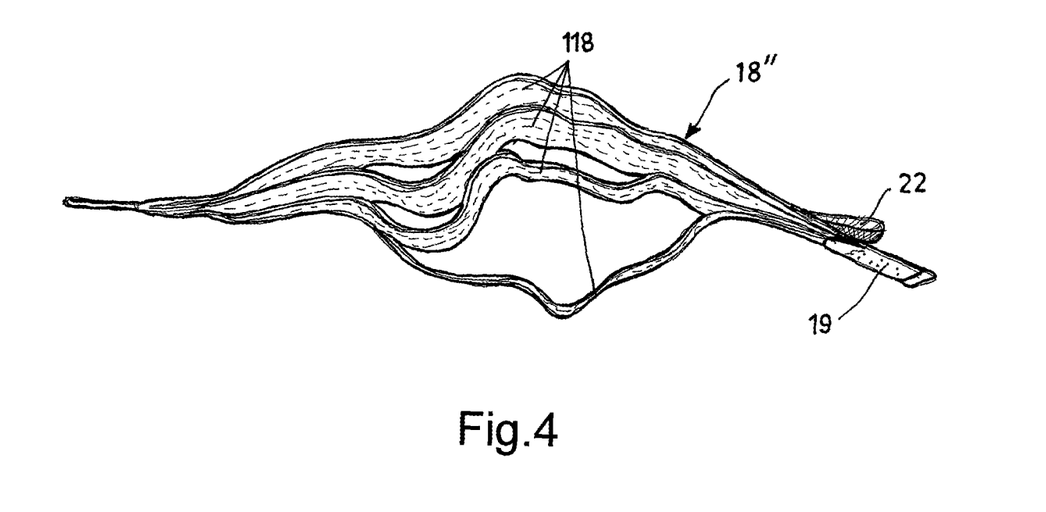
FIG. 4 shows an elastic pulling strip that can be applied to a brace according to the invention.

This feature is preferably obtained by joining in parallel a plurality of elastic bands 118 sewed together at the opposite ends in order to make a single elastic band that constitutes the elastic pulling strip 18". The example of FIG. 4 shows, by way of example, an elastic pulling strip 18" consisting of four elastic bands 118.

Moreover, in order to facilitate the grip on the pulling strip 18" by the patient or by the health worker, each pulling strip 18" comprises a gripping element 22 placed at one end that is adapted to be arranged frontally on the brace 10 worn. Similarly, also the ends of the lumbar band 14a and of the thigh band 14b are provided with gripping elements.

Figure 5:
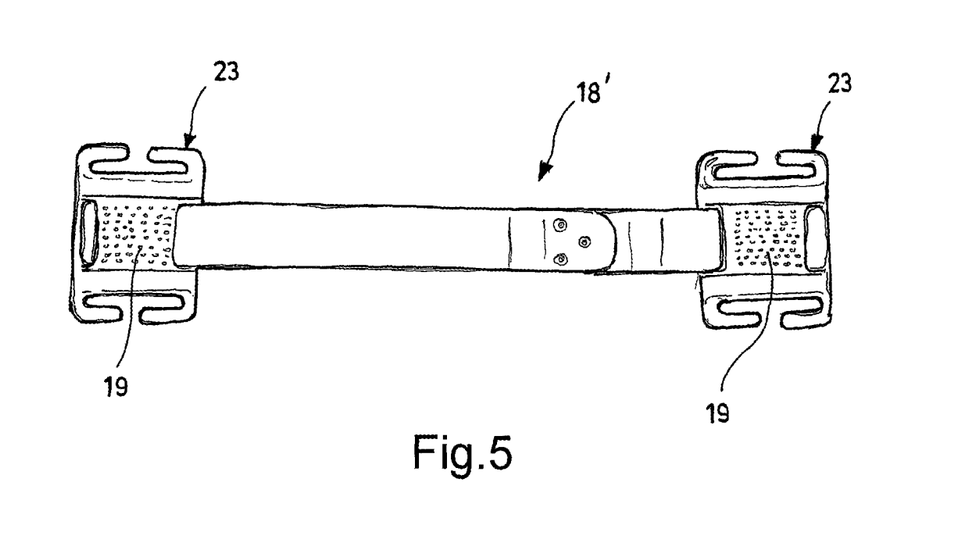
FIG. 5 shows an articulated rod that can be applied to a brace according to the invention.
Figure 6A:
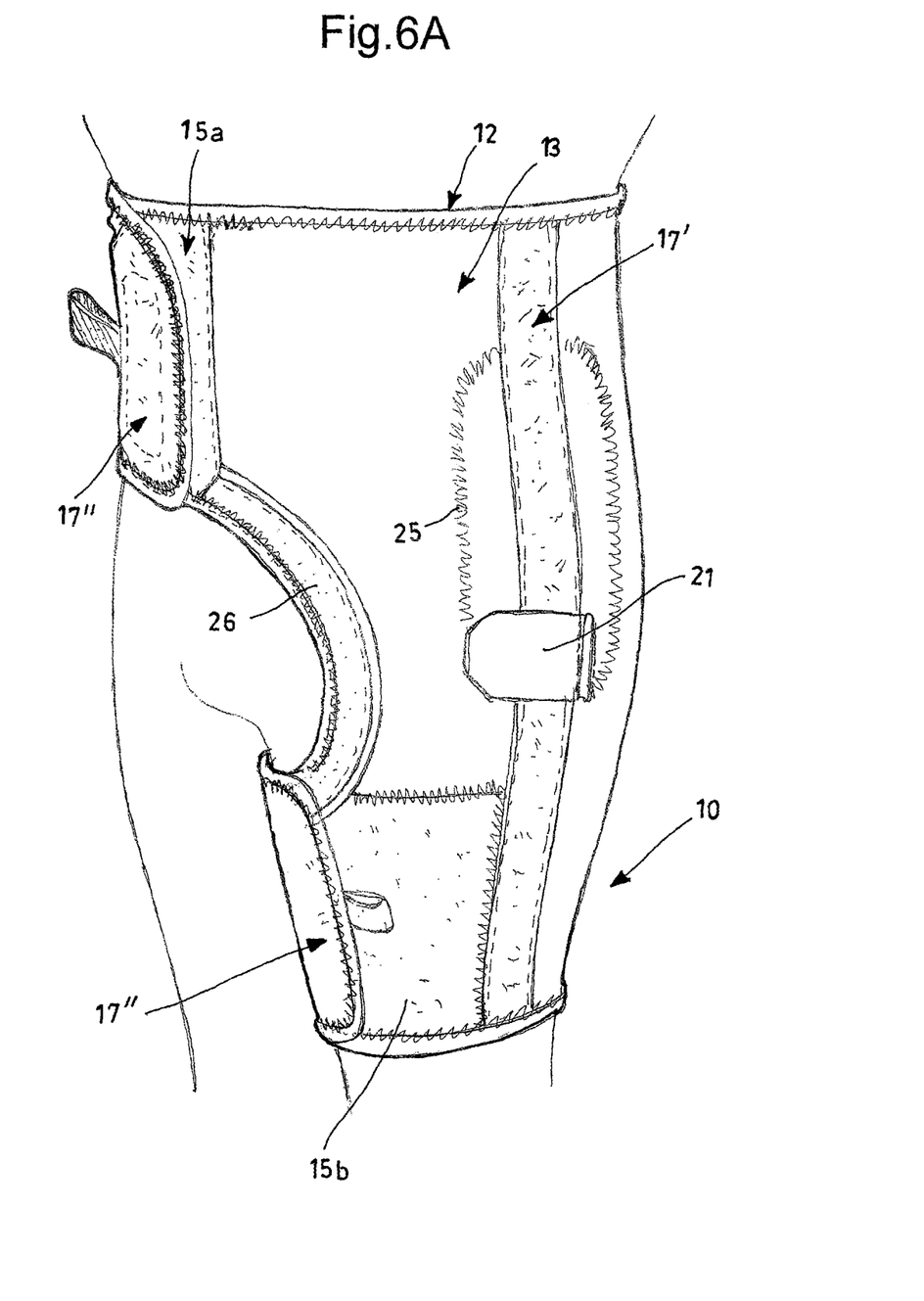
FIGS. 6A, 6B, 6C and 6D show the hip brace of the invention in the use configuration, respectively without the application of any additional accessory, with the application of a pair of elastic pulling strips, with the application of an articulated rod or with the simultaneous application of both additional accessories.
Figure 6B:
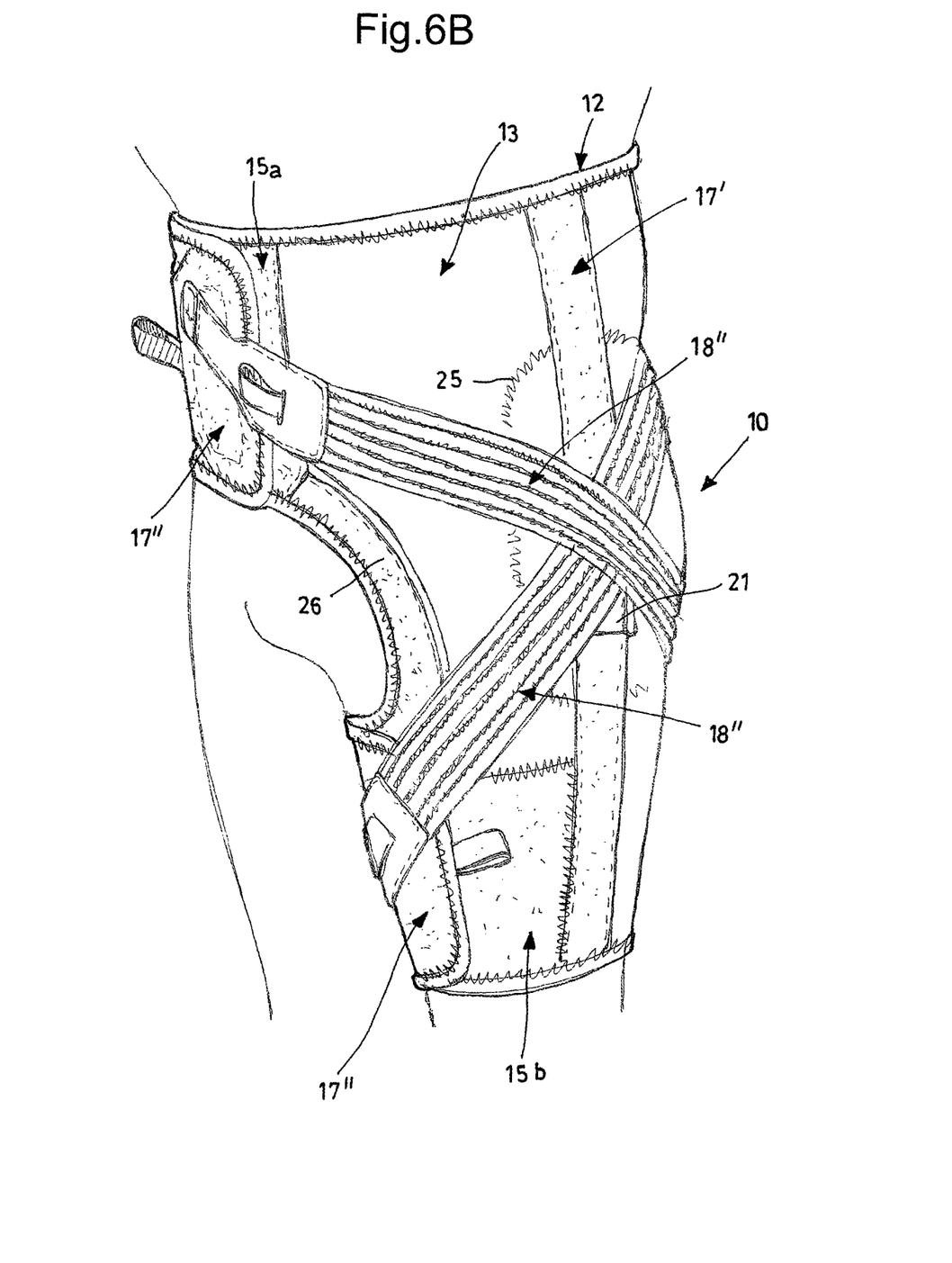
Figure 6C:
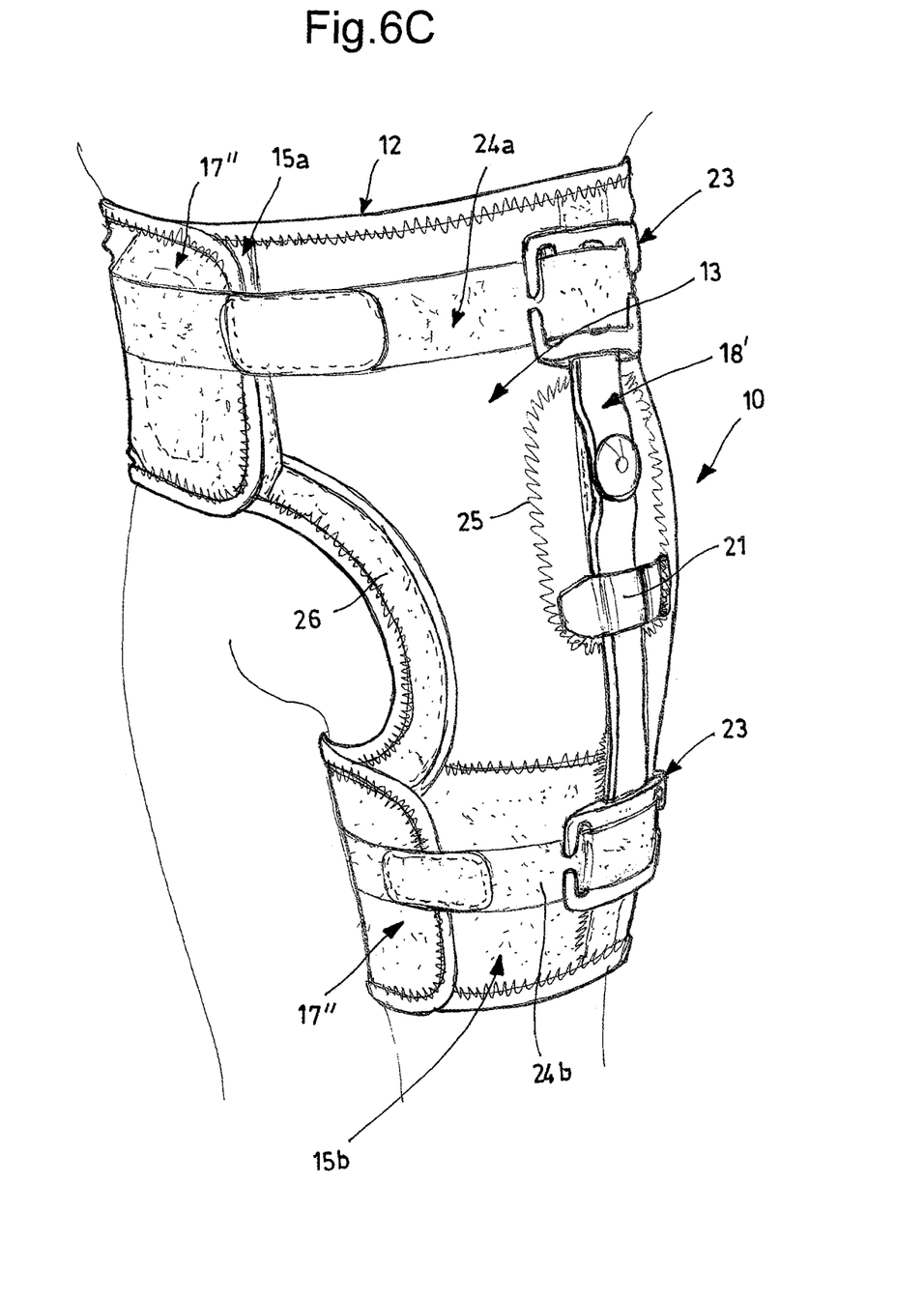
Figure 6D:
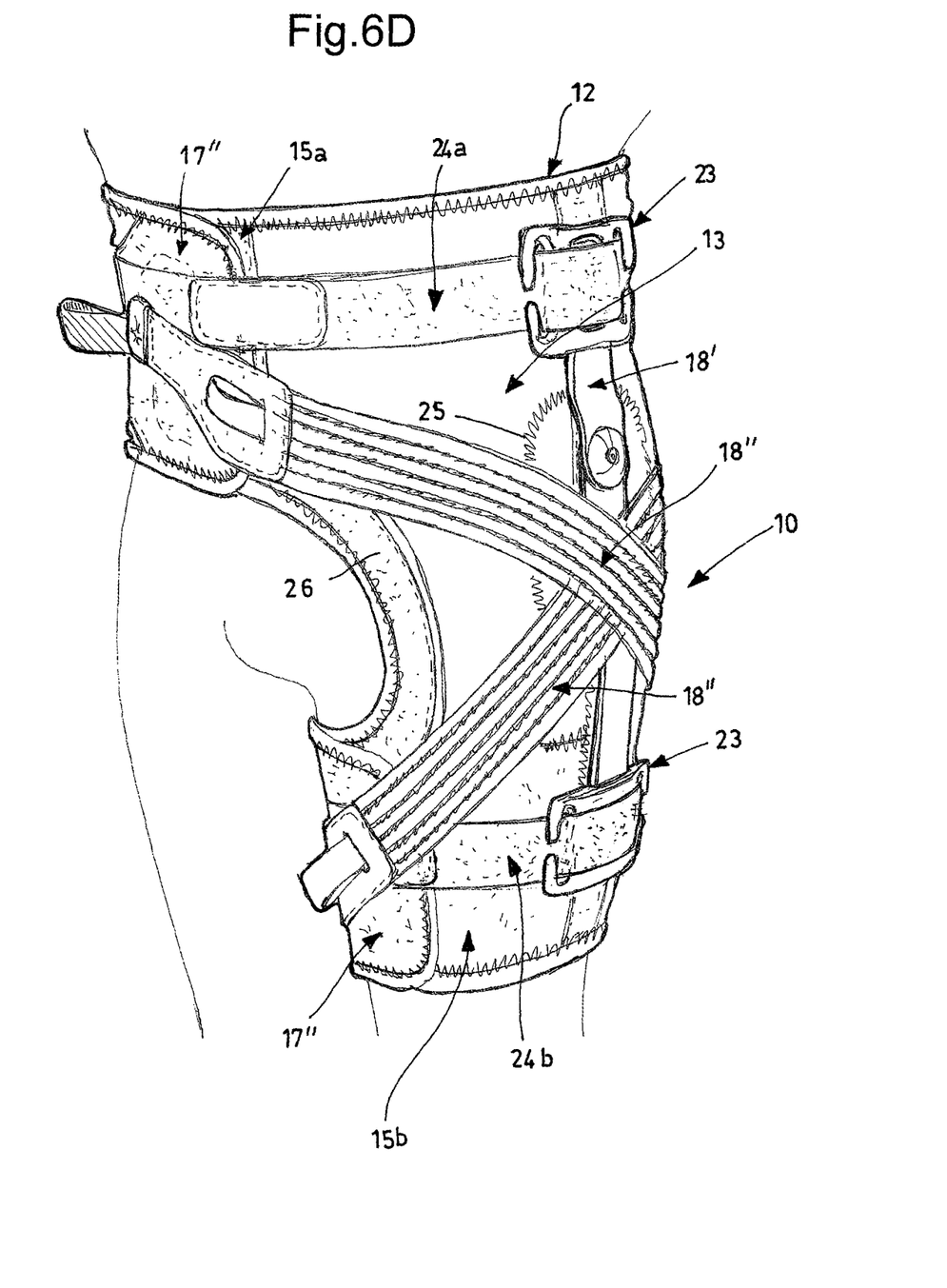

According to one embodiment of the brace 10 shown by way of non-limiting example, the articulated rod 18', shown in FIG. 5, is provided at opposite ends with a buckle element 23, each adapted to cooperate with a lumbar belt 24a and with a thigh belt 24b, which can be wrapped on the lumbar band 14a and on the thigh band 14b respectively (FIGS. 6C and 6D). Furthermore, the buckle element 23 preferably bears quick hooking means 19, shown of the Velcro® type. According to an alternative embodiment, the opposite ends of the articulated rod 18' could be removably inserted in pockets arranged in the side portion 13, not shown.

According to one embodiment of the brace 10 shown by way of non-limiting example, the side portion 13 comprises, on the inner side, a pocket 25 for the cryotherapeutic treatment, adapted to receive a cooling element, not shown, such as a gel bag for the treatment of pain and edema.

In the hip brace 10 according to the invention, the retaining wrapping base of elastic fabric 12 comprises, along a front edge, i.e. facing frontally, a curved stay 26, arranged parallel to the edge between the lumbar band 14a and the thigh band 14b. Such a curved stay 26 is aimed at keeping the brace 10 in the correct position around the thigh when the patient is sitting.

According to a preferred embodiment of the brace 10 according to the invention, the lumbar band 14a further comprises a reinforcement elastic element 27 sewed between the fabric portions of the front and rear hooking arrangements 17" of the lumbar band 14a, so as to be arranged along the side corresponding to the healthy leg when the brace 10 is worn (FIGS. 1 and 2).

The described above features of the brace 10 according to the invention can be present simultaneously, as well as taken individually.

In order to wear a brace 10, object of the invention, the same is drawn near to the leg to be treated, placing the side portion 13 against the joint to be treated and the lumbar 15a and thigh closing supports 15b on the front side. The lumbar 14a and thigh 14b bands are wrapped about the waist and about the thigh of the patient, respectively, corresponding to the joint to be treated, and constrained on the relative closing supports 15a and 15b by exerting a suitable clamping force.

In order to apply the pair of elastic pulling strips 18", each of them is first rearly constrained to an upper and lower hooking arrangement 17" and then applied diagonally on the side and clamped respectively on the lower and upper hooking arrangement 17". The second elastic pulling strip 18" is positioned so as to be crossed to the first one at the side. The elastic pulling strips 18" have the dual function of preventing/reducing the hip adduction on the one side, and of slightly limiting the flexion-extension.

In order to apply the articulated rod 18', the same is constrained by means of the quick hooking means on the side of the side portion 13 and held in position both by means of the central through 21 and by means of the two belts 24a and 24b inserted in the buckle elements 23 at the ends of the articulated rod 18' and circumferentially clamped on the lumbar band 14a and on the thigh band 14b, respectively. The articulated rod 18' has a function similar to that of the elastic pulling strips 18", but through a rigid element, which allows a controlled flexion movement, for example generally from 0° to 80° or even wider, such as for instance from 0° to 120°, sub-intervals included.

According to what is schematically shown in FIGS. 6A, 6B, 6C and 6D, the hip brace 10 object of the invention has a plurality of different application configurations. In fact, it can be used without the application of any additional accessory, with the application of the pair of elastic pulling strips 18", with the application of the articulated rod 18' or with the simultaneous application of both additional accessories.

The different configurations exert a different containment and limitation extent of the movement and are adapted both to the different conditions of different patients and also to modify the type of rehabilitation treatment for the same patient, by modulating it over time.

The hip brace 10 object of the present invention advantageously ensures two different degrees of restraint:
- a retaining base for exerting a slight pressure capable of reducing edema and possibly of providing a cold therapy step,
- an additional element for selectively limiting movements (abduction and flexion-extension) in order to protect the joint subjected to surgery from the risk of dislocation.

As regards the abduction/adduction of the limb, it has been seen that often in the post-surgery period, an adductor contracture occurs (probably due to a pain-protective and compensatory mechanism), which may facilitate the dislocation, a problem that the brace 10 object of the invention aims at solving by exerting a minimum of stabilization. For this reason, the brace 10 will therefore requires a 3 thrust-point system (as shown by the arrows F in FIG. 1), which "prevents" or retains the hip adduction. In particular, it has been seen that it is not necessary to position the joint in forced abduction, but it is sufficient to prevent the joint from going beyond the "neutral position".

With regard to the flexion-extension of the limb, it has been seen that the sitting position is more risky than the standing one for dislocation. The brace must give a minimum stabilization in flexion (a sort of proprioceptive feedback may be sufficient) with a progressive limitation of the same, in order not to make the patient reach a position (for example beyond 80° or 120° of flexion) that is potentially at a risk of dislocation. This will of course not happen during the normal walking steps, instead when having to sit.

The brace object of the invention also provides for easy accessibility to the surgical site for medical treatments, without excessively rigid/angular elements both in the most common case of anterior and antero-lateral surgical access and in the case of postero-lateral surgical access.

Moreover, it is advantageously possible for the physical therapist to adjust the action of the brace so as to provide a containment and limitation action of the movement that is differentiated over time and according to specific needs, having all of the functionalities required thanks to a single product.

The multifunctional hip brace thus conceived can undergo several changes and variations, all falling within the invention; moreover, all details can be replaced with technically equivalent elements. In practice, the materials used as well as the sizes, can be any, according to the technical needs.

The invention claimed is:

1. A multifunctional hip brace comprising:
   a retaining wrapping base of elastic fabric comprising a side portion, a lumbar band and a thigh band,
   wherein said lumbar band and said thigh band are placed at opposite ends of said side portion and can be wrapped about the waist and about a thigh of the patient and can be clamped in adjustable positions through quick hooking means,
   wherein said side portion is entirely made of fabric,
   wherein the hip brace further comprises additional accessory elements to selectively limit the movements of the hip,
   wherein said elastic retaining wrapping base comprises a plurality of arrangements for hooking the additional accessory elements,
   the additional accessory elements hooked by said plurality of arrangements include an articulated rod, which is externally constrained in a removable manner to said side portion through quick hooking means, and a pair of elastic pulling strips, which are externally constrained in a removable manner through quick hooking means, the pair of elastic pulling strips being diagonally placed between said lumbar band and said thigh band in a position crossed to one another, and
   wherein said plurality of arrangements for hooking said additional accessory elements are arranged longitudinally along said side portion and frontally and ready on said lumbar band and on said thigh band.

2. The hip brace according to claim 1, wherein said plurality of arrangements includes second arrangements for hooking said pair of elastic pulling strips, and said second arrangements comprise fabric portions for adhesion of said quick hooking means of said pair of elastic pulling strips, said fabric portions being provided with indicators of an area for the adhesion.

3. The hip, brace according to claim 2, wherein said lumbar band comprises a reinforcement elastic element sewed between said second arrangements for the frontal and rear hooking of said lumbar band.

4. The hip brace according to claim 1, wherein said plurality of arrangements includes first arrangements for hooking said articulated rod, and said first arrangements comprise fabric portions for the adhesion of said quick hooking means of said articulated rod and a central through.

5. The hip brace according to claim 1, wherein each elastic pulling strip comprises a plurality of elastic bands sewed to one another in parallel at opposite ends in order to make an elastic band.

6. The hip brace according to claim 1, wherein said articulated rod is provided at opposite ends with a buckle element that cooperates with a lumbar belt and with a thigh belt, which can be respectively wrapped on said lumbar band and on said thigh band.

7. The hip brace according to claim 1, wherein said side portion comprises, on an inner side, a pocket for a cryotherapeutic treatment.

8. The hip brace according to claim 1, wherein said retaining wrapping base of elastic fabric comprises, along a front edge, a curved stay arranged parallel to the front edge.

* * * * *